United States Patent [19]

Tsuji et al.

[11] Patent Number: 5,106,854
[45] Date of Patent: Apr. 21, 1992

[54] QUINOLINECARBOXYLIC ACIDS

[75] Inventors: Teruji Tsuji, Osaka; Hisao Sato, Nara; Tetsuo Okada, Osaka, all of Japan

[73] Assignee: Shionogi & Co., Ltd., Osaka, Japan

[21] Appl. No.: 631,171

[22] Filed: Dec. 13, 1990

Related U.S. Application Data

[63] Continuation of Ser. No. 361,865, Jun. 6, 1989, abandoned.

[30] Foreign Application Priority Data

Jun. 21, 1988 [JP] Japan .................. 63-152593
Mar. 10, 1989 [JP] Japan .................... 1-58809

[51] Int. Cl.⁵ .................... C07D 401/10; A61K 31/47
[52] U.S. Cl. ..................................... 514/312; 546/156
[58] Field of Search ..................... 546/156; 514/312

[56] References Cited

U.S. PATENT DOCUMENTS

| | | | |
|---|---|---|---|
| 4,556,658 | 12/1985 | Grohe et al. | 514/254 |
| 4,705,788 | 11/1987 | Schriewer et al. | 546/156 |
| 4,771,055 | 9/1988 | Domagala et al. | 514/312 |
| 4,927,926 | 5/1990 | Corominas et al. | 546/156 |
| 4,990,517 | 2/1991 | Petersen et al. | 546/156 |

FOREIGN PATENT DOCUMENTS 0172651  2/1986  European Pat. Off. .

Primary Examiner—Cecilia Shen
Assistant Examiner—Philip Datlow
Attorney, Agent, or Firm—Wenderoth, Lind & Ponack

[57] ABSTRACT

Novel quinolonecarboxylic acids of the formula:

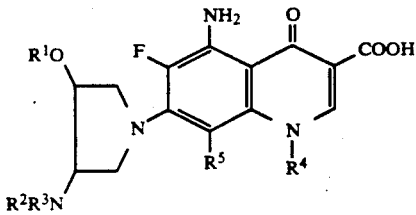

wherein $R^1$ is $C_1$-$C_4$ alkyl, $R^2$ and $R^3$ each is identically or differently hydrogen or $C_1$-$C_4$ alkyl, $R^4$ is cyclopropyl, phenyl, halo-phenyl, or thienyl optionally substituted by $C_1$-$C_4$ alkyl or halogen, and $R^5$ is halogen, or pharmaceutically acceptable salts thereof having a more potent and longer lasting antibacterial activities against G(+) and G(−) bacteria than known analogues, useful as antibacterial agents at an oral dose of 1-500 mg, preferably 50-100 mg per day to an adult.

6 Claims, No Drawings

QUINOLINECARBOXYLIC ACIDS

This application is a continuation of now abandoned application, Ser. No. 07/361,865 filed on June 6, 1989.

BACKGROUND OF THE INVENTION

1. Field of the Invention

The present invention relates to novel quinolonecarboxylic acids exhibiting excellent antibacterial activities against gram-positive and gram-negative bacteria.

2. Prior Art

The compounds described in U.S. Pat. No. 4,382,892, FR. Pat. No. 2,563,521 and U.S. Pat. No. 4,528,287 Specifications have been known as pyridonecarboxylic acid antibacterial agents. Many of these known products have problems such as induction of adverse effect like convulsions when administered to humans. Consequently, the aim of this invention is to supply antibacterial agents having strong antibacterial activity together with reduced CNS adverse reactions such as convulsions.

SUMMARY OF THE INVENTION

This invention relates to quinolonecarboxylic acids. Compounds of the present invention have, at the 7-position, a substituent possessing two asymmetric carbons. The scope of this invention extends to the optically active compounds or racemic ones of the formula (I) inclusive of cis-forms and trans-forms.

DETAILED DESCRIPTION

The present invention relates to compounds of the formula:

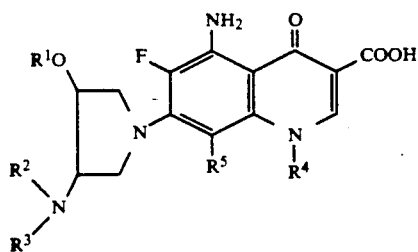

wherein $R^1$ is $C_1$-$C_4$ alkyl, $R^2$ and $R^3$ each is identically or differently hydrogen or $C_1$-$C_4$ alkyl, $R^4$ is cyclopropyl, phenyl, halogeno-phenyl, or thienyl which is optionally substituted by $C_1$-$C_4$ alkyl or halogen, and $R^5$ is halogen, or its pharmaceutically acceptable salts thereof.

In this invention, $C_1$-$C_4$ alkyl means straight or branched chain $C_1$-$C_4$ alkyl, including methyl, ethyl, n-propyl, isopropyl, n-butyl, sec-butyl, isobutyl, tert-butyl, and the like.

Halogen means chlorine, bromine, fluorine, or iodine.

The compound (I) of this invention can be prepared by the following Method A or B.

Method A

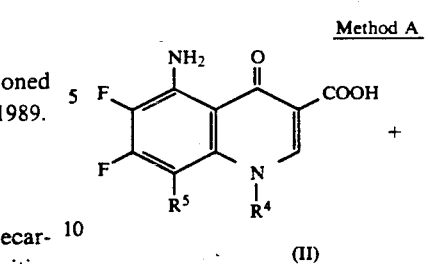

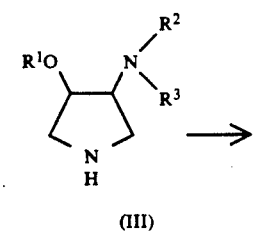

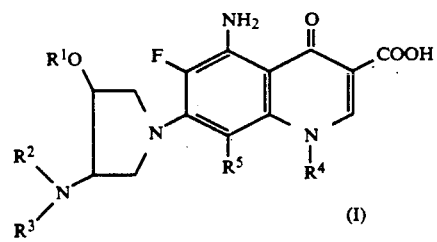

wherein $R^1$, $R^2$, $R^3$, $R^4$ and $R^5$ have the same meanings as defined above.

Starting materials (II) can be prepared by the process described in U.S. Pat. No. 4,382,892.

The compound (I) of this invention can be prepared by reacting the starting material (II) with the amine (III). This reaction can be performed in a solvent such as water, an alcohol, acetonitrile, dimethyl sulfoxide (DMSO) or dimethylformamide (DMF). The reaction is performed at a temperature between 15°-200° C., preferably between 80°-120° C. or around the boiling point of the solvent for one to several hours.

Method B

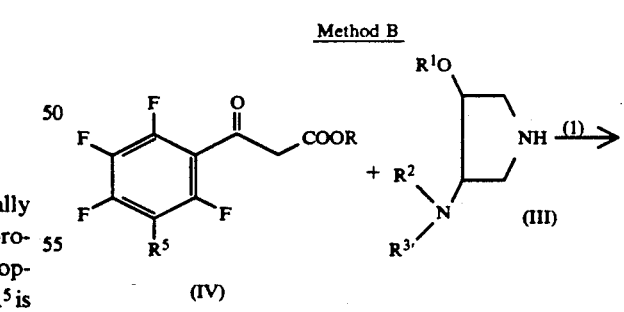

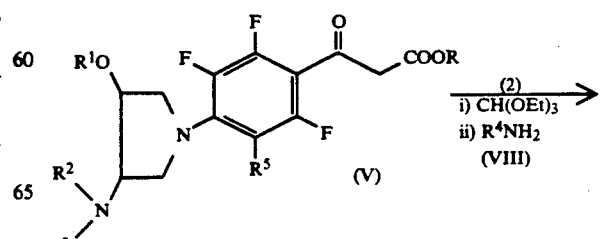

-continued
Method B

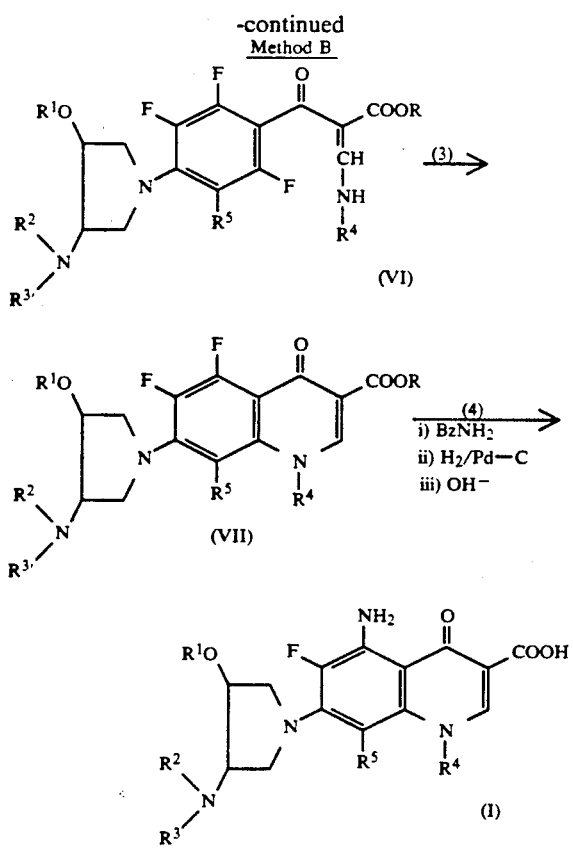

wherein R means hydrogen or $C_1-C_4$ alkyl, $R^{3'}$ means amino-protecting group, and $R^3$, $R^4$ and $R^5$ have the same meaning as defined above.

Amino-protecting group means acyl such as formyl, acetyl, or propionyl.

(1) The compound (V) can be prepared by reacting the starting material (IV) with the amine (III). This reaction can be performed in a solvent such as acetonitrile, dimethyl sulfoxide (DMSO), dimethylformamide (DMF), an alcohol or tetrahydrofuran (THF). The reaction is performed at a temperature from 0° C. to around the boiling point of the solvent. In order to expedite the reaction, an inorganic base such as sodium carbonate, potassium carbonate, sodium hydroxide or potassium hydroxide or an organic base such as DBU, triethyl amine and the like may be used in a conventional manner.

(2) The compound (VI) can be prepared by reacting the compound (V) with ethyl orthoformate and condensing the resultant formyl compound with the amine $R^4NH_2$ (VIII). The former reaction is performed in acetic anhydride at a temperature from 80° C. to around the boiling point of acetic anhydride. The condensation is performed in a solvent such as ethanol, acetone, dimethyl sulfoxide or dioxane at a temperature from 0° C. to 50° C., preferably around room temperature (15°–30° C.).

(3) The compound (VII) can be prepared by the treatment of the compound (VI) with a base in a solvent such as DMF, THF, DMSO or acetonitrile at a temperature from 0° C. to around the boiling point of the solvent. As the base, an alkaline metal hydride such as sodium hydride or potassium hydride, or an organic amine such as triethyl amine or pyridine may be used in a conventional manner.

(4) The compound (VII) is allowed to react with benzylamine to introduce the benzylamino group at the 5-position, and then the benzyl group is removed by catalytic hydrogenation. Thus, the introduction of benzylamino group is performed in a solvent such as acetonitrile, DMF or DMSO in a sealed tube at a temperature from 80° to 150° C. The hydrogenation is performed in a solvent such as methanol, ethanol, acetic acid or acetonitrile over a catalyst such as Pd-C at a temperature from 0° to 50° C., preferably around room temperature under atmospheric pressure in a conventional manner.

If necessary, any amino-protecting groups such as carbobenzoxy, trityl or ethoxycarbonyl on the pyrrolidine ring or any carboxy-protecting group may be deprotected in a conventional manner.

The compounds of the formula (I) can be converted to acid-addition salts thereof in a conventional manner, if deseired. The salt-forming acid illustratively includes an inorganic acid such as hydrochloric acid, sulfuric acid or phosphoric acid and an organic acid such as methanesulfonic acid, lactic acid, oxalic acid or acetic acid.

The compounds of this invention may also be led to salts with alkaline metal such as sodium or potassium.

Illustration examples of the compounds (I) are shown below.

(1) (+)-1-Cyclopropyl-5-amino-6,8-difluoro-1,4-dihydro-7-(cis-3-methylamino-4-methoxy-1-pyrrolidinyl)-4-oxo-3-quinolinecarboxylic acid.

(2) (−)-1-Cyclopropyl-5-amino-6,8-difluoro-1,4-dihydro-7-(cis-3-methylamino-4-methoxy-1-pyrrolidinyl)-4-oxo-3-quinolinecarboxylic acid.

(3) (+)-1-Cyclopropyl-5-amino-6,8-difluoro-1,4-dihydro-7-(cis-3-amino-4-methoxy-1-pyrrolidinyl)-4-oxo-3-quinolinecarboxylic acid.

(4) (−)-1-Cyclopropyl-5-amino-6,8-difluoro-1,4-dihydro-7-(cis-3-amino-4-methoxy-1-pyrrolidinyl)-4-oxo-3-quinolinecarboxylic acid.

(5) 1-Cyclopropyl-5-amino-6,8-difluoro-1,4-dihydro-7-(cis-3-amino-4-methoxy-1-pyrrolidinyl)-4-oxo-3-quinolinecarboxylic acid.

(6) 1-(2,4-Difluorophenyl)-5-amino-6,8-difluoro-1,4-dihydro-7-(cis-3-methylamino-4-methoxy-1-pyrrolidinyl)-4-oxo-3-quinolinecarboxylic acid.

(7) 1-Thienyl-6,8-difluoro-5amino-1,4-dihydro-7-(cis-3-methyl-amino-4-methoxy-1-pyrrolidinyl)-4-oxo-3-quinolinecarboxylic acid.

(8) 1-Cyclopropyl-5-amino-6,8-difluoro-1,4-dihydro-7-(cis-3-methylamino-4-ethoxy-1-pyrrolidinyl)-4-oxo-3-quinolinecarboxylic acid.

(9) 1-Cyclopropyl-5-amino-8-chloro-6-fluoro-1,4-dihydro-7-(cis-3-amino-4-methoxy-1-pyrrolidinyl)-4-oxo-3-quinolinecarboxylic acid.

(10) 1-Cyclopropyl-5-amino-8-chloro-6-fluoro-1,4-dihydro-7-(cis-3-methylamino-4-methoxy-1-pyrrolidinyl)-4-oxo-3-quinolinecarboxylic acid.

(11) 1-Cyclopropyl-5-amino-6,8-difluoro-1,4-dihydro-7-(cis-3-methylamino-4-methoxy-1-pyrrolidinyl)-4-oxo-3-quinolinecarboxylic acid.

The compounds (I) of this invention can be administered orally or parenterally to humans or mammals. They can be formulated into tablets, capsules, pills, granules, injections, suppositories, and syrups by conventional pharmaceutical practice. The pharmaceutically acceptable carriers, diluents, and fillers include lactose, cane sugar, wheat starch, potato starch, magnesium stearate, gelatin, methyl cellulose, agar, water, etc. Stabilizers, emulsifiers, wet extenders, buffers, and other auxiliaries may be added thereto, if necessary. Suitable daily dosage for an adult is 1-500 mg orally and 0.1-300 mg parenterally in a single or divided doses.

The following examples, reference examples and formulation are shown to clarify the practical embodiments of this invention.

The abbreviations used in the examples and reference examples shall have the following meanings:
Me: METHYL
Et: ethyl
Bz: benzyl
MeOH: methanol
THF: tetrahydrofuran
DMF: dimethylformamide
DMSO: dimethyl sulfoxide
DBU: 1,8-diazabicyclo[5,4,0]undec-7-ene.

EXAMPLE 1

(+)-1-Cyclopropyl-5-amino-6,8-difluoro-1,4-dihydro-7-(cis-3-methylamino-4-methoxy-1-pyrrolidinyl)-4-oxo-3-quinolinecarboxylic acid hydrochloride (I-1)

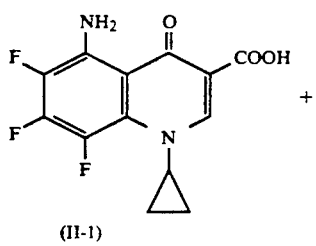

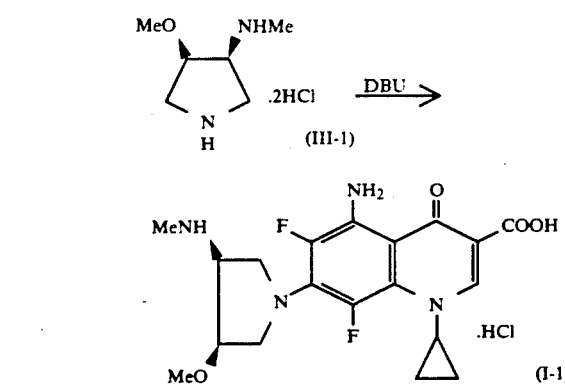

A mixture of 298 mg (1.00 mM) of the compound (II-1), 305 mg of (+)-cis-3-methylamino-4-methoxy-1-pyrrolidine hydrochloride and 600 μl of DBU is refluxed in 3 ml of acetonitrile for 1 hour. The resulting crystals are collected by filtration and washed with acetonitrile to give 345 mg of crystals (mp. 250°-251° C., dec.). The crude product is treated with 1 ml of 2 N-HCl and recrystallized from methanol-ethanol to give 358 mg of the hydrochloride (I-1) as yellow crystals. mp. 260°-263° C. (dec.).

$[\alpha]_D^{25} + 361.1° \pm 4.0°$ (c=1.004, H$_2$O).

Anal Calcd. of I-1 (%) for C$_{19}$H$_{23}$N$_4$O$_4$F$_2$Cl.½H$_2$O: C, 50.28; H, 5.33; N, 12.34; F, 8.37; Cl, 7.81. Found (%): C, 50.44; H, 5.59; N, 12.16; F, 7.34; Cl, 7.60.

NMR (200M, CD$_3$OD) δ: 1.15 (m, 4H); 2.82 (s, 3H); 3.53 (s, 3H); 3.8~4.1 (m, 6H); 4.27 (br, s, 1H); 8.53 (s, 1H).

EXAMPLE 2

(−)-1-Cyclopropyl-5-amino-6,8-difluoro-1,4-dihydro-7-(cis-3-methylamino-4-methoxy-1-pyrrolidinyl)-4-oxo-3-quinolinecarboxylic acid hydrochloride (I-2)

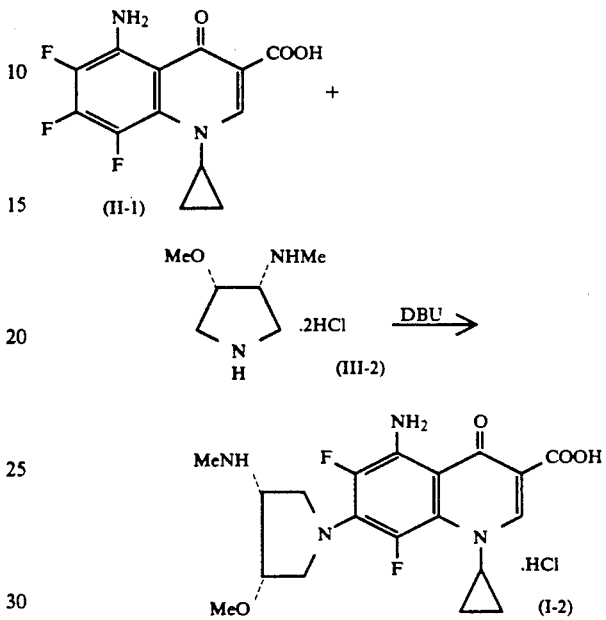

A mixture of 298 mg (1.00 mM) of the compound (II-1), 305 mg of (−)-cis-3-methylamino-4-methoxy-1-pyrrolidine hydrochloride and 600 μl of DBU is allowed to react in 4 ml of acetonitrile in the same manner as in Example 1 to give 352 mg of crystals (mp. 251°-253° C. dec.). The crude product is treated in the same manner as Example 1 to give 350 mg of the hydrochloride (I-2) as yellow crystals. mp. 264°-266° C. (dec.)

$[\alpha]_D^{25} - 364.8° \pm 4.1°$ (c=1.004, H$_2$O).

Anal Calcd. of I-2 (%) for C$_{19}$H$_{23}$N$_4$O$_4$F$_2$Cl.½H$_2$O: C, 50.28; H, 5.33; N, 12.34; F, 8.37; Cl, 7.81. Found (%): C, 50.56; H, 5.58; N, 12.22; F, 7.94; Cl, 7.40.

EXAMPLE 3

(+)-1-Cyclopropyl-5-amino-6,8-difluoro-1,4-dihydro-7-(cis-3-amino-4-methoxy-1-pyrrolidinyl)-4-oxo-3-quinolinecarboxylic acid hydrochloride (I-3)

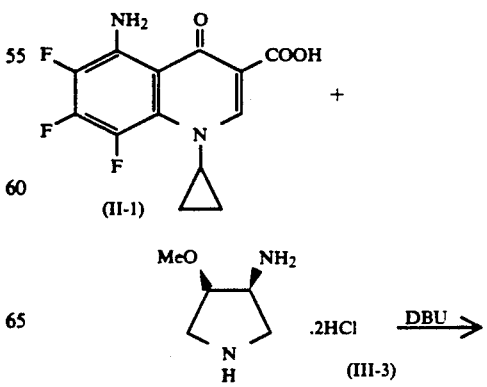

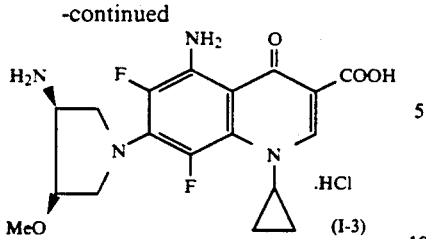

A mixture of 298 mg (1.00 mM) of the compound (II-1), 284 mg of (+)-cis-3-amino-4-methoxy-1-pyrrolidine hydrochloride (III-3) and 600 μl of DBU is refluxed in 3 ml of acetonitrile for 1 hour. The resulting crystals are collected by filtration and washed with acetonitrile to give 352 mg of crystals (mp. 243°–245° C.). The resulting product is treated with 1 ml of 2N-HCl and recrystallized from ethanol to give 342 mg of the hydrochloride (I-3) as yellow crystals. mp. 260°–263° C. (dec.).

$[\alpha]_D^{25} + 287.2° \pm 1.6°$ (c=2.013, H$_2$O).

Anal Calcd. of I-3 (%) for $C_{18}H_{21}N_4F_2Cl \cdot H_2O$: C, 48.17; H, 5.16; N, 12.48; F, 8.47; Cl, 7.90. Found (%): C, 48.26; H, 5.20; N, 12.51; F, 8.08; Cl, 7.81.

NMR (200M, CD$_3$OD): 1.15 (m, 4H); 3.52 (s, 3H); 3.8–4.1 (m, 6H); 4.22 (br, s, 1H); 8.15 (s, 1H).

EXAMPLE 4

(−)-1-Cyclopropyl-5-amino-6,8-difluoro-1,4-dihydro-7-(cis-3-amino-4-methoxy-1-pyrrolidinyl)-4-oxo-3-quinolinecarbxylic acid hydrochloride (I-4)

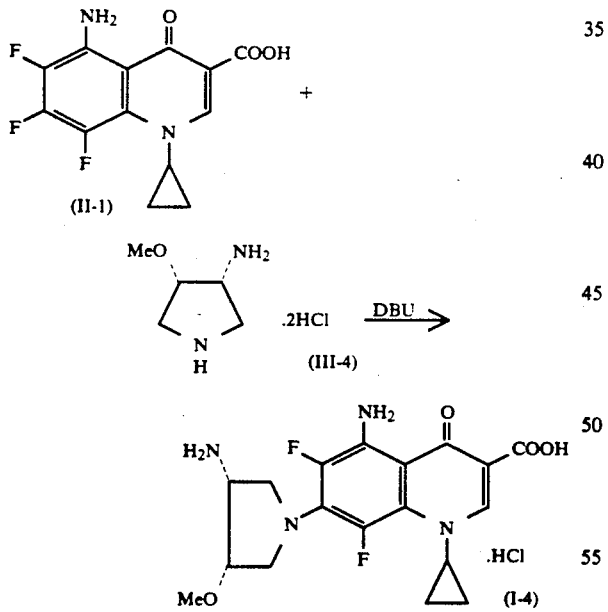

A mixture of 298 mg (1.00 mM) of the compound (II-1), 284 mg of (−)-cis-3-amino-4-methoxy-1-pyrrolidine hydrochloride (III-4) and 600 μl of DBU is allowed to react in 3 ml of acetonitrile in the same manner as in Example 3 to give 343 mg of crystals (mp. 242°–244° C.). The resulting product is treated in the same manner as in Example 3 to give 310 mg of the hydrochloride (I-4) as yellow crystals. mp. 261°–263° C. (dec.).

$[\alpha]_D^{25} - 286.3° \pm 1.6°$ (c=2.005, H$_2$O).

Anal Calcd. of I-4 (%) for $C_{18}H_{21}N_4F_2Cl \cdot H_2O$: C, 48.17; H, 5.16; N, 12.48; F, 8.47; Cl, 7.90. Found (%): C, 48.10; H, 5.21; N, 12.46; F, 7.95; Cl, 7.62.

EXAMPLE 5

1-Cyclopropyl-5-amino-6,8-difluoro-1,4-dihydro-7-(cis-3-amino-4-methoxy-1-pyrrolidinyl)-4-oxo-3-quinolinecarboxylic acid (I-5)

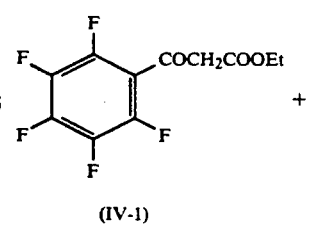

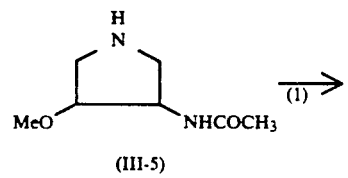

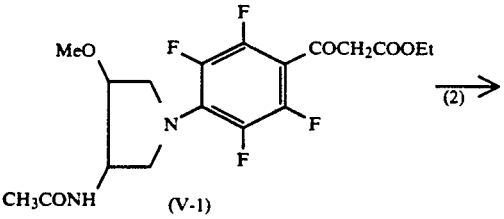

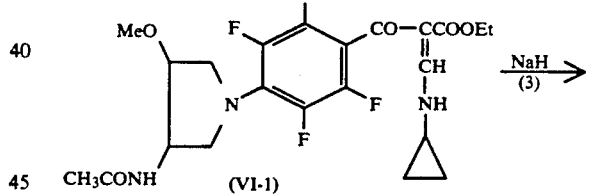

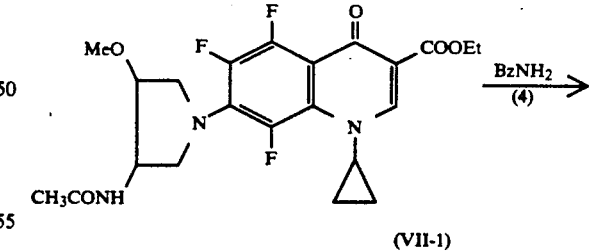

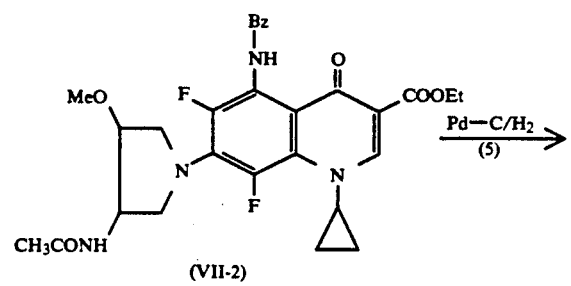

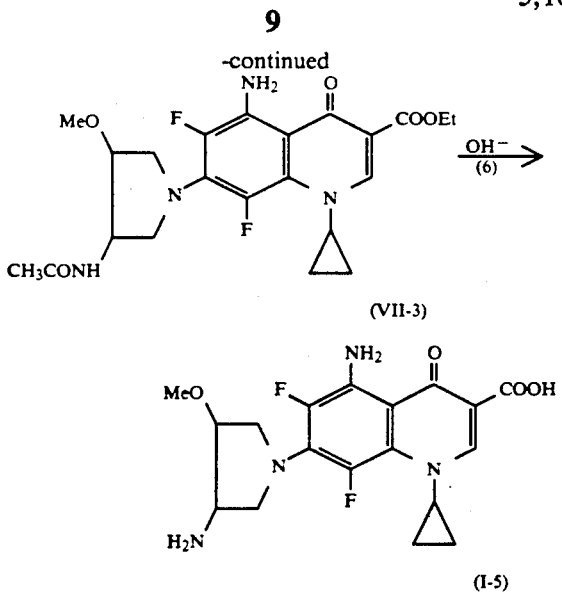

(1) A mixture of 1.8 g (11.4 mmol) of cis-3-acetoamino-4-methoxypyrrolidine (III-5), 958 mg of NaHCO$_3$ and 3.22 g (11.4 mmol) of ethyl 2,3,4,5,6-pentafluorobenzoylacetate (IV-1) is stirred in 20 ml of acetonitrile and refluxed for 1 hour. After removing the solvent, the residue is dissolved in methylene chloride and washed with water, and the solution is dried over magnesium sulfate and concentrated. The residue is treated with ether, and the resulting crystals are collected by filtration to give 2.80 g of the compound (V-1). mp. 145°-146° C.

Anal Calcd. (%) for C$_{18}$H$_{20}$N$_2$O$_5$F$_4$: C, 51.11; H, 4.74; N, 6.69; F, 18.08. Found (%): C, 51.43; H, 4.80; N, 6.66; F, 18.08.

NMR (200M, CDCl$_3$): 1.27 (t, J=7 Hz, 3H); 2.05 (s, 3H); 3.42 (s, 3H); 3.64 (m, 1H); 3.8–4.1 (m, 6H); 4.20 (q, J=7 Hz, 2H); 4.55 (m, 1H); 6.08 (d, J=8 Hz, 1H).

(2) A mixture of 1.5 g (3.57 mmol) of the compound (V-1), 832 μl of ethyl orthoformate and 674 μl of acetic anhydride is refluxed for 2 hours and the reaction mixture is concentrated under reduced pressure. The residue is mixed with a solution of 1.0 ml of cyclopropylamine in 5 ml of ethanol and stirred at room temperature for 20 minutes, and the reaction mixture is concentrated under reduced pressure. The crude product is subjected to chromatography (toluene:ethyl acetate=2:1 v/v) of Lobar Column B ® and recrystallized from ethanol to give 1.10 g (Yield: 95%) of the compound (VI-1). m.p. 175°-176° C.

Anal Calcd. (%) for C$_{22}$H$_{25}$N$_3$O$_5$F$_4$: C, 54.14; H, 5.35; N, 8.53; F, 15.20. Found (%): C, 54.32; H, 4.97; N 8.65; F, 15.62.

NMR (200M, CDCl$_3$) δ: 0.8-1.0 (m, 4H); 1.00 (t, J=7 Hz, 0.6H); 1.14 (t, J=7 Hz, 2.4H); 2.00 (s, 3H); 2.98 (m, 1H); 3.40 (s, 2.4H); 3.41 (s, 0.6H); 3.5–3.9 (m, 6H); 4.04 (q, J=7 Hz, 0.4H); 4.09 (q, J=7 Hz, 1.6H); 4.55 (m, 1H); 6.08 (d, J=8 Hz, 1H); 8.24 (d, J=15 Hz, 0.8H); 8.26 (d, J=15 Hz, 0.2H)

(3) To a stirred solution of 630 mg of the compound (VI-1) in 3 ml of DMF is added 60 mg of 60% NaH at room temperature and the mixture is stirred for 10 minutes. The reaction mixture is mixed with 7 ml of 0.5N-HCl, and the resulting crystals are collected by filtration, washed with water and dissolved in methylene chloride. The solution is dried over MgSO$_4$ and concentrated, and the residue is treated with ethyl acetate. The resulting crystals are collected by filtration to give 594 mg (Yiled: 97.8%) of the compound (VII-1). mp. 234°-235° C.

Anal Calcd. (%) for C$_{22}$H$_{24}$N$_3$O$_5$F$_3$: C, 56.51; H, 5.30; N, 9.03; F, 12.66. Found (%): C, 56.53; H, 5.18; N, 8.99; F, 12.19.

NMR (200M, CDCl$_3$) δ: 1.0–1.3 (m, 4H); 1.38 (t, J=7 Hz, 3H); 2.07 (s, 3H); 3.44 (s, 3H); 3.6–4.0 (m, 6H); 4.36 (q, J=7 Hz, 2H); 3.60 (m, 1H); 6.27 (d, J=8 Hz, 1H); 8.40 (s, 1H).

(4) A mixture of 500 mg (1.07 mM) of the compound (VII-1), 470 μl of Et$_3$N and 180 μl of benzylamine is poured into 4 ml of acetonitrile, and the solution is stirred in a sealed tube at 130° C. for 3 hours. The reaction mixture is concentrated under reduced pressure to dryness and the residue is dissolved in methylene chloride. The solution is washed with 0.5N-HCl, dried over MgSO$_4$ and concentrated. The residue is treated with ethyl acetate and the resulting crystals are collected by filtration to give 589 mg (Yield: 99.3%) of the compound (VII-2). mp. 191°-192° C.

Anal Calcd. (%) for C$_{29}$H$_{32}$N$_4$O$_5$F$_2$: C, 62.50; H, 5.97; N, 9.87; F, 6.74. Found (%): C, 62.81; H, 5.82; N, 10.10; F, 6.85.

NMR (200M, CDCl$_3$) δ: 0.9-1.3 (m, 4H); 1.37 (t, J=Hz, 3H); 2.04 (s, 3H); 3.39 (s, 3H); 3.5–3.9 (m, 7H); 4.35 (q, J=7 Hz, 2H); 4.52 (m, 1H); 4.54 (d, J=3 Hz, 2H); 6.13 (d, J=8 Hz, 1H); 7.2–7.4 (m, 5H); 8.35 (s, 1H).

(5) To a mixture of 7 ml of acetic acid and 7 ml of ethanol are added 459 mg (0.83 mM) of the compound (VII-2) and 80 mg of 5% Pd-C, and the resulting mixture is hydrogenated at room temperature under atmospheric pressure and filtered. The filtrate is concentrated under reduced pressure and the residue is dissolved in methylene chloride. The organic layer is washed with water, dried over MgSO$_4$ and concentrated. The residue is treated with ethyl acetate and the resulting crystals are collected by filtration to give 318 mg (Yield: 82.7%) of the compound (VII-3). mp. 199°-201° C.

Anal Calcd. (%) for C$_{22}$H$_{26}$N$_4$O$_6$F$_2$: C, 56.93; H, 5.66; N, 11.82; F, 8.08. Found (%): C, 56.89; H, 5.64; N, 12.06; F, 8.18.

NMR (200M, CDCl$_3$) δ: 0.9-1.2 (m, 4H); 1.38 (t, J=7 Hz, 3H); 2.06 (s, 3H); 3.42 (s, 3H); 3.5–4.0 (m, 6H); 4.36 (q, J=7 Hz, 2H); 4.59 (m, 1H); 6.17 (d, J=8 Hz, 1H); 8.36 (s, 1H)

(6) 1.5 ml of 2N-NaOH solution containing 100 mg (0.22 mM) of the compound (VII-3) is stirred in a sealed tube at 110° C. for 5 hours. The reaction mixture is mixed with 1.5 ml of 2N.HCl and 1 drop of 28% aqueous ammonia and concentrated under reduced pressure. The residue is extracted with acetonitrile, and the organic layer is concentrated. The resulting crystals are collected by filtration to give 54 mg (Yield: 63.6%) of the objective compound (I-5). mp. 222°-223° C.

Anal Calcd. (%) for C$_{18}$H$_{20}$N$_4$O$_4$F$_2$: C, 54.34; H, 5.04; N, 14.01; F, 9.19. Found (%): C, 54.82; H, 5.11; N, 14.21; F, 9.63.

NMR (200M, DMSO) δ: 1.0-1.2 (m, 4H); 3.36 (s, 3H); 3.4–4.1 (m, 7H); 8.45 (s, 1H)

EXAMPLE 6

1-(2,4-Difluorophenyl)-5-amino-6,8-difluoro-1,4-dihydro-7-(cis-3-methylamino-4-methoxy-1-pyrrolidinyl)-4-oxo-3-quinolinecarboxylic acid hydrochloride (I-6)

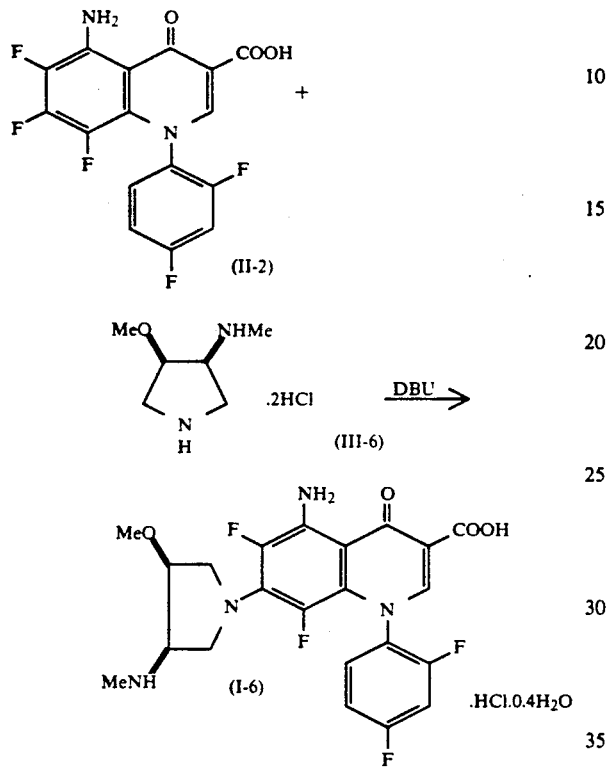

A solution of 100 mg of 1-(2,4-difluorophenyl)-5-amino-6,7,8-trifluoro-1,4-dihydro-4-oxo-3-quinolinecarboxylic acid (II-2), 102 mg of the compound (III-6) and 76 mg of DBU in 20 ml of DMSO is heated in oil bath for 2 hours. The reaction mixture is concentrated under reduced pressure, and the residue is mixed with water and the resulting crystals are collected by filtration. Since the starting compound (II-2) is contained in this crude product to about one third, the additional reaction is carried out by adding 102 mg of the compound (III-6) and 76 mg of DBU to the crude product, dissolving the mixture in 20 ml of DMSO and heating it at 100° C. on oil bath for 2 hours. The reaction mixture is worked up as described above. The resulting crystals are washed with ether and dried to give 90 mg of crude product. This product is treated with 2 ml of 36% c-HCl at room temperature. The reaction mixture is concentrated under reduced pressure and the resulting residue is treated with acetone for crystallization. The resulting crystals are filtered to give 90 mg of the hydrochloride (I-6) as yellow crystals.

mp. over 290° C. (dec.)

IR $\nu_{max}^{Nujol}$: 3420, 3300 (NH), 1730, 1630 cm$^{-1}$.

$^1$HNMR (200 MHz, DMSO) δ: 2.12 (s, 3H, N—CH$_3$); 2.59 (s, 3H, OCH$_3$); 7.2-8.1 (m, 3H); 8.43 (s, 1H, C$_2$—H).

Anal Calcd. (%) for C$_{22}$H$_{20}$N$_4$O$_4$F$_4$.HCl.0.4H$_2$O: C, 50.42; H, 4.19; N, 10.69; F, 14.49; Cl, 6.76. Found (%): C, 50.67; H, 4.45; N, 10.70; F, 14.16; Cl, 6.54.

EXAMPLE 7

1-Thienyl-6,8-difluoro-5-amino-1,4-dihydro-7-(cis-3-methyl-amino-4-methoxy-1-pyrrolidinyl)-4-oxo-3-quinolinecarboxylic acid hydrochloride (I-7)

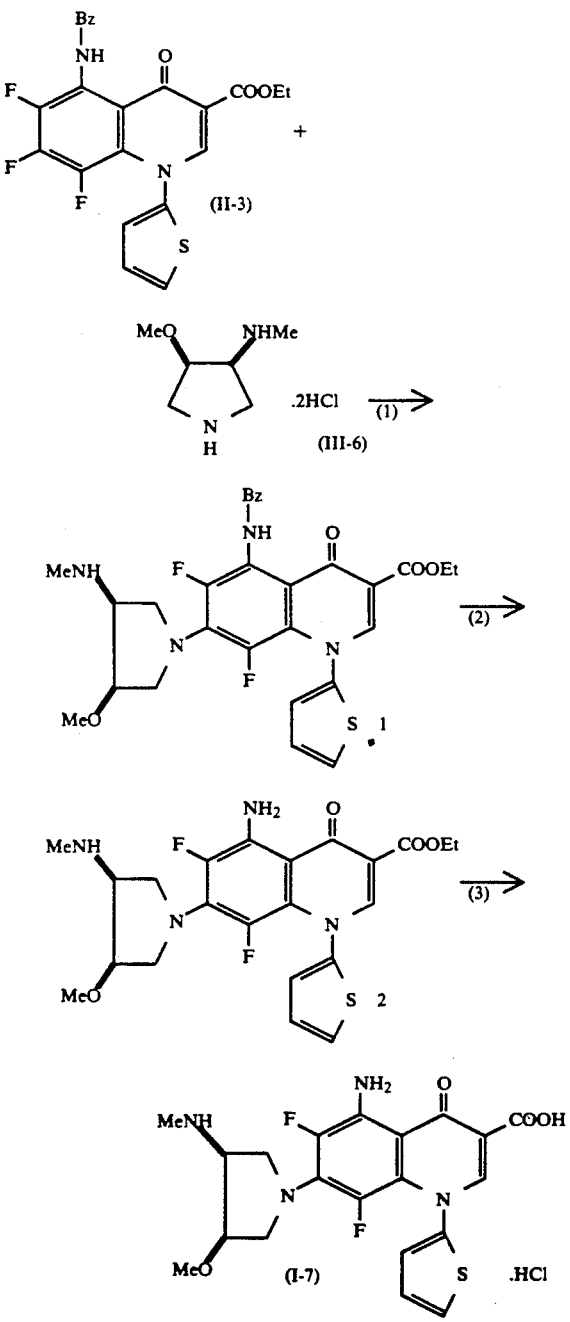

(1) A mixture of 500 mg of ethyl 1-thienyl-5-benzylamino-6,7,8-trifluoro-1,4-dihydro-4-oxo-3-quinolinecarboxylate (II -3), 443 mg of the compound (III -6), 331 mg of DBU and 10 ml of DMSO is heated on oil bath for 3 hours. The reaction mixture is concentrated under reduced pressure, and the residue is chromatographed on a column of silica gel, eluting with chloroform and methanol (50:1 v/v). The eluate is concentrated to give 120 mg (Yield: 19%) of the objective compound 1.

NMR (200 MHz, CDCl₃) δ: 1.37 (t, J=7 Hz, 3H, —CH₂CH₃); 2.46 (s, 3H, —NHCH₃); 3.36 (s, 3H, —OCH₃); 3.0–4.8 (m); 4.37 (q, J=7 Hz, 2H, —CH₂CH₃); 3.0–4.7 (m); 6.9–7.5 (m); 8.15 (s, 1H, C₂—H).

(2) To a solution of 80 mg of the compound 1 in 20 ml of methanol are added 40 mg of 10% Pd-C and 2 ml of 2N-HCl, and the mixture is hydrogenated at room temperature under 5 atmospheric pressure of hydrogen gas for 7 hours. The solution is filtered with sellaite to exclude Pd-C and the filtrate is concentrated under reduced pressure. The residue is dissolved in chloroform and the solution is washed with saturated NaHCO₃. The chloroform layer is chromatographed on a column of silica gel, eluting with chloroform and methanol (10:1 v/v). The eluate is concentrated to give 26 mg (Yiled: 39%) of the compound 2 as foamy residue.

IR $\nu_{max}^{CHCl_3}$: 3500, 3300 (—NH₂), 1722, 1698, 1630 cm⁻¹.

NMR (200M, CDCl₃) δ: 1.36 (t, J=7 Hz, 3H): 2.46 (s, 3H, —NHCH₃); 3.37 (s, 3H, —OCH₃); 3.0–4.0 (m); 4.35 (q, J=7 Hz, 2H); 6.5–7.3 (m); 8.15 (s, 1H, C₂—H).

(3) A mixture of 26 mg of the compound 2, 1 ml of 2N-HCl, 2 ml of ethanol and 2 ml of water is heated on oil bath at 100° C. for 1 hour. After cooling, the mixture is concentrated under reduced pressure and the residue is treated with methanol. After removing the insolble matter, the filtrate is concentrated. The resulting residue is crystallized from acetone and filtered to give 18 mg (Yield: 75%) of the hydrochloride (I-7). mp. 280°–285° C. (dec.)

IR $\nu_{max}^{Nujol}$: 3420, 3300, 1730, 1640 cm⁻¹.

NMR (200 MHz, D₂O) δ: 2.82 (s, 3H, —NHCH₃); 3.44 (s, 3H, —OCH₃); 3.4–4.4 (m); 7.0–7.6 (m); 8.40 (s, 1H, C₂—H).

EXAMPLE 8

1-Cyclopropyl-5-amino-6,8-difluoro-1,4-dihydro-7-(cis-3-methylamino-4-ethoxy-1-pyrrolidinyl)-4-oxo-3-quinolinecarboxylic acid hydrochloride (I-8)

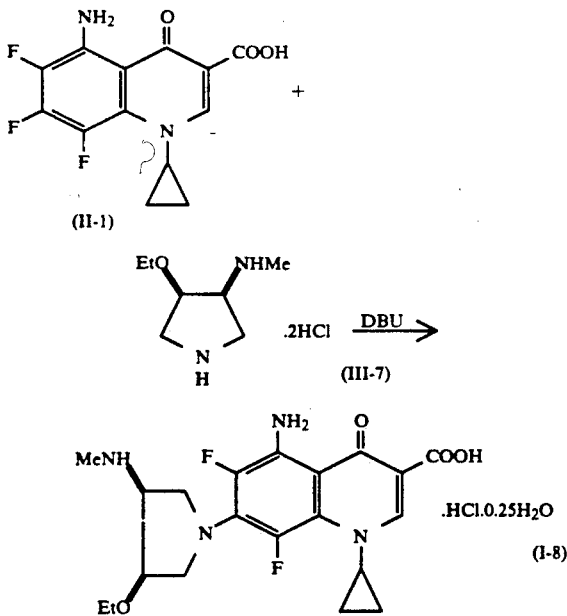

To a suspension of 2.30 g (7.71 mM) of the compound (II-1) in 70 ml of dry acetonitrile are added 2.842 g of the compound (III-7) and 4.61 ml of DBU, and the reaction mixture is stirred on oil bath at 100° C. for 1.5 hours. After cooling the mixture, the resulting crystals are collected by filtration to give 2.971 g (Yield: 91.2%) of yellow crystals. The crystals are dissolved in a mixture of 7 ml of 2N-HCl and 2.3 ml of c-HCl and the solution is concentrated under reduced pressure. The resulting residue is mixed with 50 ml of ethanol, and the solution is allowed to leave overnight at 5° C. The resulting crystals are collected by filtration and recrystallized from water-ethanol-acetone to give 3.102 mg of the hydrochloride (I -8) as yellow crystals. mp. 278°–286° C. (dec.)

Anal Calcd. (%) for C₂₀H₂₄N₄O₄F₂.HCl.0.25H₂O: C, 51.84; H, 5.55; N, 12.09; F, 8.20; Cl, 7.65. Found (%): C, 51.84; H, 5.71; N, 12.08; F, 7.75; Cl, 7.28.

EXAMPLE 9

1-Cyclopropyl-5-amino-8-chloro-6-fluoro-1,4-dihydro-7-(cis-3-amino-4-methoxy-1-pyrrolidinyl)-4-oxo-3-quinolinecarboxylic acid (I -9)

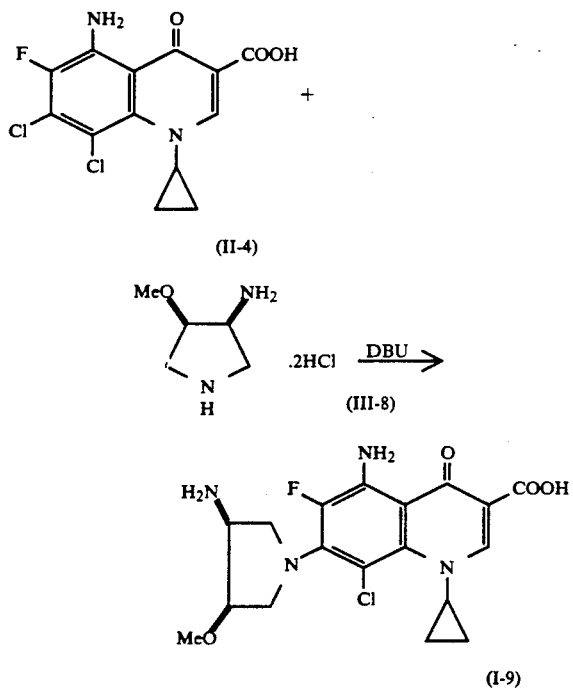

To a solution of 188 mg (0.6 mmol) of 1-cyclopropyl-5-amino-8-chloro-6,7-difluoro-1,4-dihydro-4-oxo-3-quinolinecarboxylic acid (II -4) in 4 ml of acetonitrile are added 231 mg (1.8 mmol) of the compound (III -8) and 122 mg (1.2 mmol) of triethylamine. The reaction mixture is refluxed for 3 hours. After cooling, the resulting crystals are collected by filtration. The crude crystals are recrystallized from methylene chloride-methanol-ethyl acetate to give 153 mg (Yield: 60.2%) of 1-cyclopropyl-5-amino-8-chloro-6-fluoro-7-(cis-3-methylamino-4-methoxy-1-pyrrolidinyl)1,4-dihydro-4-oxo-3-quinolinecarboxylic acid (I -9). mp. 206°–207° C.

Anal Calcd. (%) for C₁₉H₂₂ClFN₄O₄: C, 53.71; H, 5.22; Cl, 8.34; F, 4.47; N, 13.19. Found (%): C, 53.79; H, 5.11; Cl, 8.38; F, 4.58; N, 13.28.

IR (Nujol): 3396, 3272, 1728, 1630, 1605 cm⁻¹.

NMR (DMSO-d₆) δ: 8.65 (1H, s, 2-H); 7.7–7.3 (2H, br, NH, COOH); 4.35 (1H, m, —C₃H₆); 3.98 (2H); 3.56

(2H); 3.35 (3H, s, OCH₃); 3.33 (2H); 2.43 (3H, s, NCH₃); 1.26–0.74 (4H, m, —C₃H₆)

EXAMPLE 10

1-Cyclopropyl-5-amino-8-chloro-6-fluoro-1,4-dihydro-7-(cis-3-methylamino-4-methoxy-1-pyrrolidinyl)-4-oxo-3-quinolinecarboxylic acid (I -10)

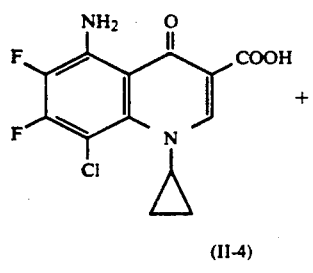

(II-4)

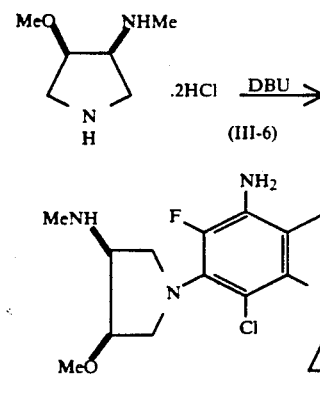

(I-10)

The compound (III -6) is allowed to react with the compound (II -4) in the same manner as in Example 9 to give 1-cyclopropyl-5-amino-8-chloro-6-fluoro-7-(cis-3-methylamino-4-methoxy-1-pyrrolidinyl)-1,4-dihydro-4-oxo-3-quinolinecarboxylic acid (I -10) (Yield: 48.8%). mp. 190°–192° C. (dec.).

Anal Calcd. (%) for C₁₈H₂₀ClFN₄O₄: C, 52.62; H, 4.91; Cl, 8.63; F, 4.62; N, 13.64. Found (%): C, 52.66; H, 4.94; Cl, 8.15; F, 4.91; N, 13.24.

IR (Nujol): 3444, 3320, 1714, 1639 cm⁻¹.

NMR (CDCl₃) δ: 8.74 (1H, s, 2-H); 7.0–6.4 (3H, br, NH₂, COOH); 4.22 (1H, m, C₃H₅); 4.0–3.6 (6H); 3.46 (3H, s, OCH₃), 1.3–0.7 (4H)

EXAMPLE 11

1-Cyclopropyl-5-amino-6,8-difluoro-1,4-dihydro-7-(cis-3-methylamino-4-methoxy-1-pyrrolidinyl)-4-oxo-3-quinolinecarboxylic acid (I -11)

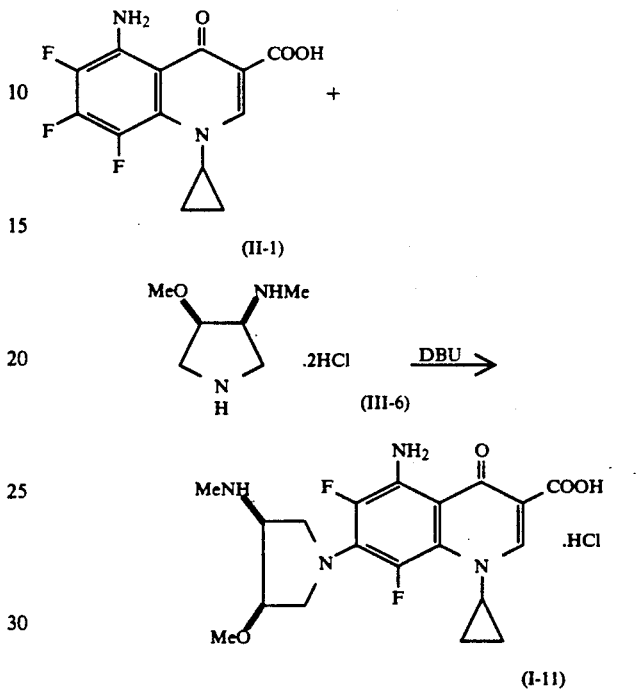

To a mixture of 320 mg (1.07 mM) of the compound (II-1) and 376 mg of the compound (III-6) are added 10 ml of acetonitrile and 0.64 ml of DBU, and the reaction mixture is refluxed on water bath for 1.5 hours. After cooling the solution, the resulting crystals are collected by filtration to give 412 mg of the compound (I-11), which is recrystallized from methanol to give 292 mg of the compound (I-11) as yellow crystals. mp. 262°–264° C. (dec.)

Anal Calcd. (%) for C₁₉H₂₂N₄O₄F₂: C, 55.88; H, 5.43; N, 13.72. Found (%): C, 55.82; H, 5.45; N, 13.56.

REFERENCE EXAMPLE 1

Cis-3-amino-4-methoxypyrrolidine

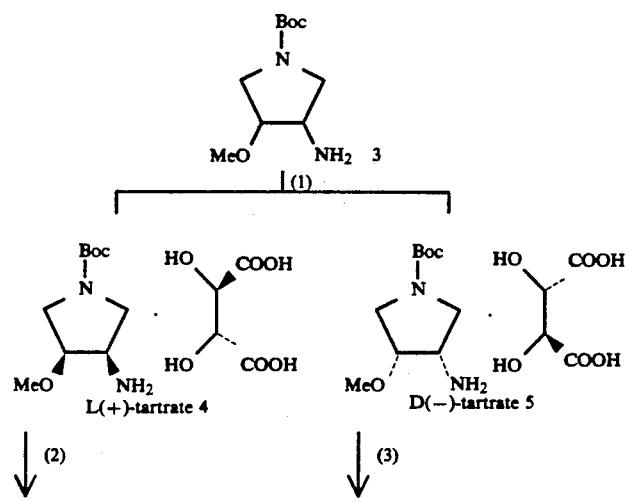

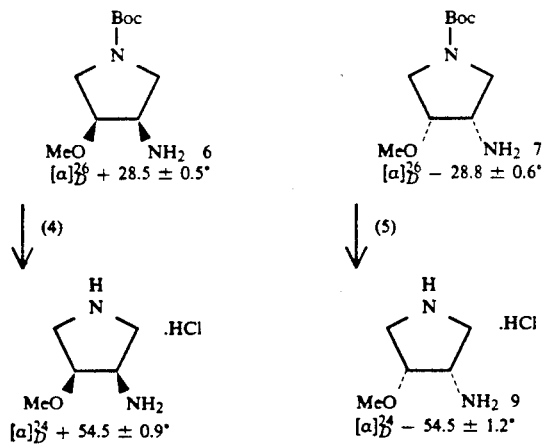

(1) A racemic mixture of 10 g of 3,4-cis-pyrrolidine compound 3 is treated with 10 g of L(+)-tartaric acid in 50 ml of methanol, and allowed to stand at room temperature for 3 hours. The resulting L(−)-tartarate is collected by filtration and recrystallized from methanol to give 6.12 g of L(+)-tartarate 4 (mp. 197°–198° C., dec.). All of the filtrates are combined and evaporated under reduced pressure. After the residue is dissolved in saturated brine, the solution is basified with $K_2CO_3$ and extracted with ethyl acetate. Then the extract is washed with saturated brine, dried over $MgSO_4$ and concentrated under reduced pressure to give 6.16 g of oily substance. Then the substance is dissolved in 40 ml of methanol. The solution is mixed with 6.0 g of D(−)-tartaric acid and left at room temperature for 3 hours. The resulting D(−)-tartarate is collected by filtration and the crystals are recrystallized from methanol to give 5.62 g of D(−)-tartarate 5 (mp. 197°–198° C., dec.). After the remaining mother liquor is treated in the same manner as described above to give L(+)-tartarate, and the crystals are recrystallized to give 0.57 g of L(+)-tartarate 4. The resulting mother liquor is treated in the same manner as described above, and mixed with D(−)-tartaric acid to give 0.37 g of D(−)-tartarate 5.

L(+)-tartarate 4:

$[\alpha]_D^{26}$ +34.1°±0.7° (c=1.015, methanol), mp. 197°–198° C. (dec.),

Anal Calcd. (%) for $C_{10}H_{20}N_2O_3 \cdot C_4H_6O_6$: C, 45.69; H, 6.96; N, 7.63. Found (%): C, 45.90; H, 7.15; N, 7.65.

D(−)-tartarate 5:

$[\alpha]_D^{26}$ +33.4°±0.7° (c=1.015, methanol).

Anal Calcd. (%) for $C_{10}H_{20}N_3O_3 \cdot C_4H_6O_6$: C, 45.76; H, 6.89; N, 7.63. Found (%): C, 45.90; H, 7.15; N, 7.65.

(2) L(+)-tartrate 4 6.10 g is treated in the same manner as described in (1) to give 3.80 g of the compound 6 as oily substance.

$[\alpha]_D^{26}$ +28.5°±0.5° (c=1.407, methanol).

NMR (200M, CDCl$_3$): 1.46 (s, 9H); 2.27 (brs, 2H); 3.1 (m, 1H); 3.40 (s, 3H); 3.3–3.6 (m, 4H); 3.7 (m, 1H).

(3) D(−)-Tartarate 5 5.60 g is treaed in the same manner as described (1) to give 3.30 g of the compound 7 as oily substance.

$[\alpha]_D^{26}$ −28.2°±0.6° (c=1.163, methanol).

NMR (200M, CDCl$_3$): 1.46 (s, 9H); 1.85 (brs, 2H); 3.1 (m, 1H); 3.40 (s, 3H); 3.3–3.6 (m, 4H); 3.7 (m, 1H).

(4) A solution of 2.0 g of the compound 6 in 3.1N-HCl in 20 ml of methanol is stirred at room temperature for 1 hour and concentrated under reduced pressure. The resulting residue is recrystallized from methanol to give 1.58 g of the compound 8 as hygroscopic crystals. mp. 207°–208° C.

$[\alpha]_D^{24}$ +54.5°±0.9° (c=1.111, methanol).

Anal Calcd. (%) for $C_5H_{14}N_2OCl_2$: C, 31.76; H, 7.46; N, 14.82; Cl, 37.50. Found (%): C, 31.43; H, 7.34; N, 14.83; Cl, 37.51.

(5) Compound 7 2.0 g is allowed to react in the same manner as in (4) to give 1.63 g of hygroscopic crystals 9. m.p. 208°–209° C.

$[\alpha]_D^{24}$ −54.4°±1.2° (c=0.814, methanol)

Anal Calcd. (%) for $C_5H_{14}N_2OCl_2$: C, 31.76; H, 7.46; N, 14.82; Cl, 37.50. Found (%): C, 30.43; H, 7.31; N, 14.58; Cl, 37.51.

REFERENCE EXAMPLE 2

Cis-3-methylamino-4-methoxypyrrolidine

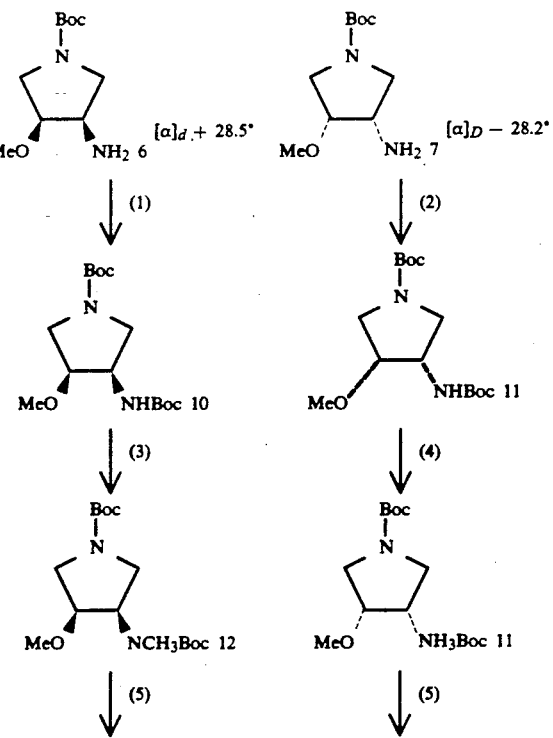

-continued

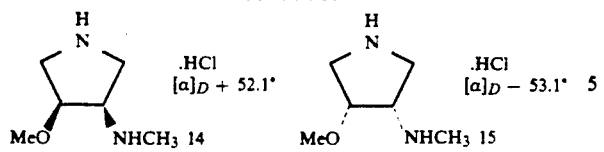

(1) To a solution of 1.50 g (6.93 mM) of the compound 6 in 10 ml of methanol is added 2.0 ml of di-tert-butyl dicarbonate and the reaction mixture is stirred for 30 minutes under ice-cooling and further 30 minutes at room temperature. The solvent is distilled off under reduced pressure, and the resulting residue is subjected to chromatography of Lobar column B ® (toluene-:ethyl acetate=4:1 v/v) to give 2.30 g of the compound 10.

(2) Compound 7 1.50 g (6.93 mM) is allowed to react in the same manner as in (1) to give 2.30 g of the compound 11.

(3) A solution of 2.20 g (6.90 mM) of the compound 10 in 10 ml of DMF is mixed with 414 mg of 60% NaH under ice-cooling, and stirred at room temperature for 15 minutes. The reaction mixture is poured into ethyl acetate, and the solution is washed with water for three times. The extract is dried over $MgSO_4$ and concentrated under reduced pressure. The residue is subjected to chromatography of Lobar column B ® (toluene-:ethyl acetate=7:1 v/v) to give 2.25 g of the compound 12.

(4) The compound 11 2.30 g (6.90 mM) is allowed to react in the same manner as in (3) to give 2.20 g of the compound 13.

(5) To 2.10 g (6.4 mM) of the compound 12 is added 60 ml of 3.1N-HCl-MeOH gradually, and the reaction mixture is stirred at room temperature for 1.5 hours and concentrated under reduced pressure. And the residue is recrystallized from ethanol to give 1.25 g of the compound 14 as hygroscopic crysals. mp. 180°-182° C.

$[\alpha]_D^{24} = 52.1° \pm 1.0°$ (c=0.973, methanol).

Anal Calcd. (%) for $C_6H_{16}N_2OCl_2$: C, 34.80; H, 7.90; N, 13.52. Found (%): C, 35.48; H, 7.94; N, 13.79.

(6) Compound 13 2.10 g (6.40 mM) is allowed to react in the same manner as in (5) to give 1.21 g of the compound 15 as hygroscopic crystals. m.p. 178°-180° C.

$[\alpha]_D^{24} - 53.1° \pm 0.9°$ (c=1.026, methanol).

EFFECT OF THE INVENTION

Experiment (Antibacterial spectrum)

The antibacterial activity was determined by measuring minimum growth inhibitory concentrations (MICs) in accordance with the method designated by the Japan Society of Chemotherapy. The results are shown in Table 1.

A, B, C and D in the table indicate the following meanings:
A: *Staphylococcus aureus* SMITH
B: *Staphylococcus aureus* SR 14 (R)
C: *Escherichia coli* EC-14
D: *Escherichia coli* SR377 (R).

The test microorganisms were used at $10^6$ cells/ml.

TABLE 1

| Compound | MICs (μg/ml) | | | |
| No. | A | B | C | D |
| --- | --- | --- | --- | --- |
| I-11 | 0.05 | 0.05 | 0.05 | 0.1 |
| I-1  | 0.1  | 0.1  | 0.1  | 0.2 |
| I-2  | 0.05 | 0.05 | 0.05 | 0.1 |
| I-5  | 0.02 | 0.05 | 0.02 | 0.05 |
| I-3  | 0.05 | 0.05 | 0.02 | 0.1 |
| I-4  | 0.02 | 0.02 | 0.02 | 0.05 |
| OFLX* | 0.2 | 0.4 | 0.1 | 0.1 |

*OFLX: ofloxacin (Reference drug)

These results have proven that the compounds of this invention show strong antibacterial activities against gram-positive and gram-negative bacteria.

What we claim is:

1. 1-Cyclopropyl-5-amino-6,8-difluoro-1,4-dihydro-7-(3-methylamino-4-methoxy-1-pyrrolidinyl)-4-oxo-3-quinolinecarboxylic acid in a free or salt form.

2. The compound according to claim 1, which is a cis form with respect to the methylamino group and the methoxy group on the pyrrolidine ring.

3. 1-Cyclopropyl-5-amino-6,8-difluoro-1,4-dihydro-7-(cis-3-methylamino-4-methoxy-1-pyrrolidinyl)-4-oxo-3-quinoline-carboxylic acid in a free or pharmaceutically acceptable salt form.

4. (+)-1-Cyclopropyl-5-amino-6,8-difluoro-1,4-dihydro-7-(cis-3-methylamino-4-methoxy-1-pyrrolidinyl)-4-oxo-3-quinoline-carboxylic acid in a free or pharmaceutically acceptable salt form.

5. (−)-1-Cyclopropyl-5-amino-6,8-difluoro-1,4-dihydro-7-(cis-3-methylamino-4-methoxy-1-pyrrolidinyl)-4-oxo-3-quinoline-carboxylic acid in a free or pharmaceutically acceptable salt form.

6. 1-Cyclopropyl-5-amino-8-chloro-6-fluoro-1,4-dihydro-7-(cis-3-methylamino-4-methoxy-1-pyrrolidinyl)-4-oxo-3-quinolinecarboxylic acid in a free or pharmaceutically acceptable salt form.

* * * * *